(12) United States Patent
Yang et al.

(10) Patent No.: US 11,487,045 B2
(45) Date of Patent: Nov. 1, 2022

(54) METHOD FOR RECOVERING POROSITY EVOLUTION PROCESS OF SEQUENCE STRATIGRAPHY OF CARBONATE ROCKS

(71) Applicant: China University of Petroleum-Beijing, Beijing (CN)

(72) Inventors: Leilei Yang, Beijing (CN); Donghua Chen, Beijing (CN); Guo Wei, Beijing (CN); Jing Hu, Beijing (CN); Weiquan Zhao, Beijing (CN); Keyu Liu, Beijing (CN); Jianliang Liu, Beijing (CN); Wei Yang, Beijing (CN); Xianglu Tang, Beijing (CN); Jin Lai, Beijing (CN)

(73) Assignee: China University of Petroleum-Beijing, Beijing (CN)

( * ) Notice: Subject to any disclaimer, the term of this patent is extended or adjusted under 35 U.S.C. 154(b) by 0 days.

(21) Appl. No.: 17/579,128

(22) Filed: Jan. 19, 2022

(65) Prior Publication Data
US 2022/0308257 A1    Sep. 29, 2022

(30) Foreign Application Priority Data
Mar. 23, 2021    (CN) .......................... 202110316880.3

(51) Int. Cl.
*G01V 11/00*    (2006.01)
*G01V 1/28*    (2006.01)
(Continued)

(52) U.S. Cl.
CPC ......... *G01V 99/005* (2013.01); *G01N 15/088* (2013.01); *G01N 33/241* (2013.01)

(58) Field of Classification Search
CPC .............. G01V 99/005; G01V 11/00; G01V 2210/661; G01V 2210/66; G01V 1/282;
(Continued)

(56) References Cited

U.S. PATENT DOCUMENTS 6,810,332 B2    10/2004    Harrison
7,092,822 B2    8/2006    Lenormand et al.
(Continued)

FOREIGN PATENT DOCUMENTS

CN    102411044 A    4/2012
CN    102759745 A    10/2012
(Continued)

OTHER PUBLICATIONS

Qian, Wendao et al., "Diagenesis and diagenetic stages prediction of Ed2 reservoir in the west of Bozhong sag," Petroleum, vol. 6, Issue 1, Mar. 2020, pp. 23-30. (Year: 2020).*
(Continued)

*Primary Examiner* — Jeffrey P Aiello
(74) *Attorney, Agent, or Firm* — Nutter McClennen & Fish LLP

(57) ABSTRACT

The present disclosure provides a method for recovering a porosity evolution process of sequence stratigraphy of carbonate rocks. The method comprises: a step of establishing a sequence stratigraphic framework of carbonate rocks; a step of dividing diagenetic stages; a step of simulating diagenesis and porosity evolution with increasing reservoir thickness and continuous superposition of multiple reservoirs during cyclic rise and fall of sea level to obtain a simulation result; and a step of calculating the porosity evolution in space over time by using the simulation result as initial values for simulation of diagenetic evolution process and simulating in stages and continuity the multi-stage diagenetic evolution process that the carbonate rock strata undergo after sediment based on the divided diagenetic stages. Compared with the traditional recovery of single reservoir porosity with time evolution, the method fully considers the superposition effect of multiple upper
(Continued)

reservoirs in the process of reservoir sedimentary-diagenesis.

6 Claims, 6 Drawing Sheets

(51) Int. Cl.
*G01V 1/30* (2006.01)
*G01V 99/00* (2009.01)
*G01N 15/08* (2006.01)
*G01N 33/24* (2006.01)

(58) Field of Classification Search
CPC ............ G01V 2210/663; G01V 1/306; G01V 2210/64; G01V 99/00; G01V 1/302; G01V 1/301; G01V 2210/642; G01V 1/50; G06F 30/20; G06F 2111/10; E21B 49/00; E21B 43/00; E21B 41/0092; G01N 33/24; G01N 33/241; G01N 15/088; G06T 17/05; G06T 2219/2021; G06T 19/20; G06T 17/20; G06N 3/08
USPC ............ 73/38, 152.05; 166/250.02; 324/303, 324/323; 367/59, 73; 702/2, 6, 11, 702/13–14; 703/2, 6, 10
See application file for complete search history.

(56) References Cited

U.S. PATENT DOCUMENTS

| | | | |
|---|---|---|---|
| 7,328,107 | B2 | 2/2008 | Strack et al. |
| 7,783,462 | B2 | 8/2010 | Landis, Jr. et al. |
| 9,322,268 | B2 | 4/2016 | Zuo et al. |
| 2008/0134760 | A1* | 6/2008 | Egermann .............. G01N 33/24 73/38 |
| 2010/0121580 | A1* | 5/2010 | Jacques ................. E21B 49/008 702/11 |
| 2017/0256366 | A1* | 9/2017 | Stucky ................. C07D 213/06 |
| 2020/0097622 | A1* | 3/2020 | Dogru .................... E21B 43/00 |
| 2020/0132869 | A1* | 4/2020 | Ba ......................... G01V 1/306 |
| 2021/0003742 | A1* | 1/2021 | Zhu ..................... E21B 49/0875 |
| 2021/0064994 | A1* | 3/2021 | Tomaru ................... G06N 3/08 |

FOREIGN PATENT DOCUMENTS

| | | |
|---|---|---|
| CN | 102778421 A | 11/2012 |
| CN | 104181092 A | 12/2014 |
| CN | 105203411 A | 12/2015 |
| CN | 105334150 A | 2/2016 |
| CN | 105865999 A | 8/2016 |
| CN | 106054248 A | 10/2016 |
| CN | 106597548 A | 4/2017 |
| CN | 107290506 A | 10/2017 |
| CN | 108344855 A | 7/2018 |
| CN | 108345962 A | 7/2018 |
| CN | 108363115 A | 8/2018 |
| CN | 108376189 A | 8/2018 |
| CN | 110501271 A | 11/2019 |
| CN | 110632666 A | 12/2019 |
| CN | 111475920 A | 7/2020 |
| CN | 111624674 A | 9/2020 |
| CN | 111694068 A | 9/2020 |
| CN | 111814364 A | 10/2020 |
| CN | 112285322 A | 1/2021 |
| CN | 112304839 A | 2/2021 |
| CN | 112526103 A | 3/2021 |
| CN | 112528226 A | 3/2021 |
| CN | 112731561 A | 4/2021 |
| CN | 113109891 A | 7/2021 |
| FR | 2931189 A1 | 11/2009 |
| JP | 2001354448 A | 12/2001 |
| WO | 2013149656 A1 | 10/2013 |

OTHER PUBLICATIONS

First Office Action and search report dated Aug. 4, 2021 for counterpart Chinese patent application No. 202110316880.3, along with English translation, 6 pages.

Supplementary search report dated Sep. 9, 2021 for counterpart Chinese patent application No. 202110316880.3, along with EN translation, 6 pages.

First search report dated Jul. 31, 2021 for counterpart Chinese patent application No. 202110316880.3, along with English translation, 9 pages.

Yang et al., "Effects of Dolomitization on Porosity during Various Sedimentation-Diagenesis Processes in Carbonate Reservoirs," Minerals vol. 10 No.6, Jun. 2020, 18 pages.

Zhong, "Research on the Late Cenozoic Seismic Overlay Sequence and Sea Level Changes on the Sunda Shelf," Chinese Doctoral Dissertation Full-text Database Basic Science, May 1, 2020, with English abstract, 146 pages.

\* cited by examiner

Using sequence stratigraphy and sedimentary petrology as a guide to recover the paleoclimate and paleo-sea level from in-depth analysis of geological, geochemical and geophysical data such as core, thin section and logging well, and identifying the sequence boundary in conjunction with the regional geological setting to establish the sequence stratigraphic framework of carbonate rocks

Determining a diagenetic sequence by thin section, scanning electron microscopy, fluid inclusion, cathodoluminescence and carbon and oxygen isotope assay analysis, determining the diagenetic evolution process of the reservoir, and determining typical diagenetic events and dividing diagenetic stages based on the degree of influence on the reservoir porosity

Simulating, based on a reactive solute transport simulation program, the diagenesis and porosity evolution with increasing reservoir thickness and continuous superposition of multiple reservoirs during cyclic rise and fall of sea level, according to a superposition pattern of carbonate rock sequence in vertical direction

Taking the simulation results in Step (3) as the initial value of diagenetic evolution process simulation, the diagenetic evolution is simulated by six successive sub-stages and the evolution of porosity over time in space is calculated.

FIG. 1

| Chronostratigraphy | | | Lithostrata | Seismic profile | Sequence strata | | Boundary property | Sedimentary facies | | Sea level change Fall rise |
|---|---|---|---|---|---|---|---|---|---|---|
| System | Series | Age | Formation | | Third order sequence | Third order system tract | | Subfacies | Microfacies | |
| Ordovician system | Middle series | 468.1Ma | Yijianfang formation | T₇⁵ | | | Uplift unconformity | | | |
| | | 470.0Ma | Yingshan formation | T₇⁸ | SQ4 | HST | | Open platform | gravel shoal, bioclastic shoal, limestone flat (algal) micrite composition cycle | |
| | | | | | | TST | Erosion unconformity | | | |
| | | 471.8Ma | | | SQ3 | HST | | | | |
| | | | | | | TST | Erosion unconformity | | | |
| | Lower series | 474.5Ma | | | SQ2 | HST | | | gravel shoal, limestone flat micrite composition cycle | |
| | | | | | | TST | Erosion unconformity | | | |
| | | 478.6Ma | | | SQ1 | HST | | Restricted platform | mainly dolostone flat dolomicrite | |
| | | | | | | TST | Erosion unconformity | | | |
| | | | Penglaiba formation | | | | | | | |

FIG. 11

METHOD FOR RECOVERING POROSITY EVOLUTION PROCESS OF SEQUENCE STRATIGRAPHY OF CARBONATE ROCKS

CROSS REFERENCE TO RELATED APPLICATIONS

This application claims the priority of the Chinese patent application No. 202110316880.3, filed on Mar. 23, 2021, which is hereby incorporated by reference in its entirety.

TECHNICAL FIELD

The present disclosure relates to the field of geological exploration and belongs to the field of research on the diagenesis of marine carbonate rock reservoirs, and more specifically, the present disclosure relates to a method for recovering a porosity evolution process of sequence stratigraphy of carbonate rocks.

BACKGROUND

Carbonate rock reservoirs are rich in oil and gas resources. In recent years, China has also discovered a number of large carbonate rock oil and gas fields, but because the carbonate rock reservoirs have undergone a long and complex diagenetic transformation, with large burial depths and complex pore evolution, the reservoirs have a strong non-homogeneity, and the degree of exploration and recognition is low. The reservoir capacity of carbonate rock oil and gas resources mainly depends on its pore development, so determining the evolution and distribution pattern of porosity in carbonate rock strata can more effectively evaluate favorable reservoirs and guide the direction for oil and gas exploration.

The porosity evolution and distribution of the reservoir are mainly influenced and controlled by both sediment process and diagenesis. Carbonate rock sediment is controlled by sea level changes, and the changes in climate, seawater chemistry and carbonate rock minerals caused by sea level changes make the reservoir non-homogeneous distribution in the vertical direction, which affects the later carbonate rock diagenesis. The existing porosity recovery methods tend to study the porosity evolution for a single reservoir, while ignoring the influence of carbonate rock sequence superposition, which cannot meet the current requirements of quality evaluation and favorable reservoir prediction for carbonate rock reservoirs.

SUMMARY

An object of the present disclosure is to provide a method for recovering a porosity evolution process of sequence stratigraphy of carbonate rocks to overcome the shortcomings of existing methods.

To achieve the above object, the present disclosure provides a method for recovering a porosity evolution process of sequence stratigraphy of carbonate rocks, wherein the method comprises:

a step of establishing a sequence stratigraphic framework of carbonate rocks;

a step of dividing diagenetic stages;

a step of simulating diagenesis and porosity evolution with increasing reservoir thickness and continuous superposition of multiple reservoirs during cyclic rise and fall of sea level to obtain a simulation result;

a step of calculating the porosity evolution in space over time by using the simulation result as initial values for simulation of diagenetic evolution process and simulating in stages and continuity the multi-stage diagenetic evolution process that the carbonate rock strata undergo after sediment.

According to some specific embodiments of the present disclosure, the method comprises recovering paleoclimate and paleo-sea level from geological, geochemical and geophysical data and identifying a sequence boundary in conjunction with a regional geological setting to establish the sequence stratigraphic framework of carbonate rocks.

According to some specific embodiments of the present disclosure, the method comprises using sequence stratigraphy and sedimentary petrology as a guide to recover the paleoclimate and paleo-sea level from geological, geochemical and geophysical data and identifying the sequence boundary in conjunction with the regional geological setting to establish the sequence stratigraphic framework of carbonate rocks.

According to some specific embodiments of the present disclosure, the geological, geochemical and geophysical data comprise core, thin section and logging information.

According to some specific embodiments of the present disclosure, the method comprises determining a diagenetic sequence by thin section, scanning electron microscopy, fluid inclusion, cathodoluminescence and carbon and oxygen isotope assay analysis, determining the diagenetic evolution process of the reservoir, and determining typical diagenetic events and dividing diagenetic stages based on the degree of influence on the reservoir porosity.

According to some specific embodiments of the present disclosure, the method comprises simulating, based on a reactive solute transport simulation program, the diagenesis and porosity evolution with increasing reservoir thickness and continuous superposition of multiple reservoirs during cyclic rise and fall of sea level, according to a superposition pattern of carbonate rock sequence in vertical direction.

According to some specific embodiments of the present disclosure, the simulation program is a numerical software for simulation of diagenetic effects.

According to some specific embodiments of the present disclosure, the simulation program is TOUGHREACT or TOUGHSTONE.

According to some specific embodiments of the present disclosure, the superposition pattern of carbonate rock sequence in vertical direction is to determine the timing of the cyclic rise and fall of the sea level, to determine the sediment thickness of the reservoir for each cycle, and to determine the sediment properties of each sequence, in conjunction with the established sequence stratigraphic framework of carbonate rocks, so as to establish a geological model to simulate the diagenesis and porosity evolution.

According to some specific embodiments of the present disclosure, the conditions of the geological model include a sea level rise and fall cycle of 2 Myr, a sediment rate of 100 m/Myr, a total simulated thickness of 400 m, and a sediment period of 8 Ma.

According to some specific embodiments of the present disclosure, the stratigraphic physical parameters of the geological model include rock porosity, rock horizontal permeability, rock vertical permeability, rock compression coefficient, rock density, rock thermal conductivity, and rock particle specific heat.

The geological model is computed using the simulation program described above.

According to some specific embodiments of the present disclosure, the method comprises:

(1) using sequence stratigraphy and sedimentary petrology as a guide to recover the paleoclimate and paleo-sea level from in-depth analysis of geological, geochemical and geophysical data such as core, thin section and logging well, and identifying the sequence boundary in conjunction with the regional geological setting to establish the sequence stratigraphic framework of carbonate rocks.

(2) determining a diagenetic sequence by thin section, scanning electron microscopy, fluid inclusion, cathodoluminescence and carbon and oxygen isotope assay analysis, determining the diagenetic evolution process of the reservoir, and determining typical diagenetic events and dividing diagenetic stages based on the degree of influence on the reservoir porosity.

(3) simulating, based on a reactive solute transport simulation program, the diagenesis and porosity evolution with increasing reservoir thickness and continuous superposition of multiple reservoirs during cyclic rise and fall of sea level, according to a superposition pattern of carbonate rock sequence in vertical direction.

(4) taking the simulation results in Step (3) as the initial value of diagenetic evolution process simulation, the multi-stage diagenetic evolution that the carbonate rock strata undergo after sedimentation is simulated in stages and continuously, and the evolution of porosity over time in space is calculated.

In summary, the present disclosure provides a method for recovering a porosity evolution process of sequence stratigraphy of carbonate rocks. The method of present disclosure has the following advantages.

(1) A method for recovering porosity evolution of carbonate rock strata with sequence superposition is proposed by combining the superposition pattern of carbonate rock reservoir sequence and the diagenetic evolution pattern, which fully considers the influence of superposition of multiple overlying reservoirs during the reservoir sediment—diagenesis, compared with the traditional recovery of porosity evolution of a single reservoir over time.

(2) It can quantitatively recover the spatial and temporal evolution and distribution of the reservoir porosity, realize the four-dimensional spatial and temporal evaluation of porosity in three-dimensional space and one-dimensional time, and reveal the formation mechanism and spatial spreading characteristics of the reservoirs.

BRIEF DESCRIPTION OF THE DRAWINGS

FIG. 1 shows a flow chart of a method for recovering a porosity evolution of carbonate rock strata with sequence superposition.

FIG. 11 is a diagram of the basis for the sequence division of the Yingshan Formation in the Tarim Basin of Example 1.

DETAILED DESCRIPTION

The implementation and the produced beneficial effects of the present disclosure will be described below in details through specific examples, which intends to help the reader better understand the substance and features of the present disclosure, and is not intended to limit the implementable scope of the present disclosure.

Example 1

(1) According to the flow of FIG. 1, for the carbonate rock of the Yingshan Formation in Shunnan area of the Tarim Basin, the sequence stratigraphic framework of carbonate rocks is established by recovering the paleoclimate and paleo-sea level from in-depth analysis of geological, geochemical and geophysical data such as core, thin section and logging well, and identifying the sequence boundary in conjunction with the regional geological setting (as shown in FIG. 11). Herein, the sequence stratigraphic framework of carbonate rocks is established based on the synthesis of chronostratigraphy, lithostratigraphy and biostratigraphy, in combination with the field outcrop profiles, drilling cores, sedimentary facies and regional tectonic movement analysis, and the sequence boundary being calibrated on the seismic profile through sequence stratigraphic analysis of typical well sections, in conjunction with review of the relevant information. Therein, the third-order sequence boundary is mainly erosional unconformity, which is a sequence unconformity boundary formed by sea level fall, mostly a superimposition of exposed sequence unconformity and transgressive onlap sequence unconformity, which mainly shows lithologic lithofacies mutation in the vertical direction, and is the main simulation object of this example.

Figure 2:
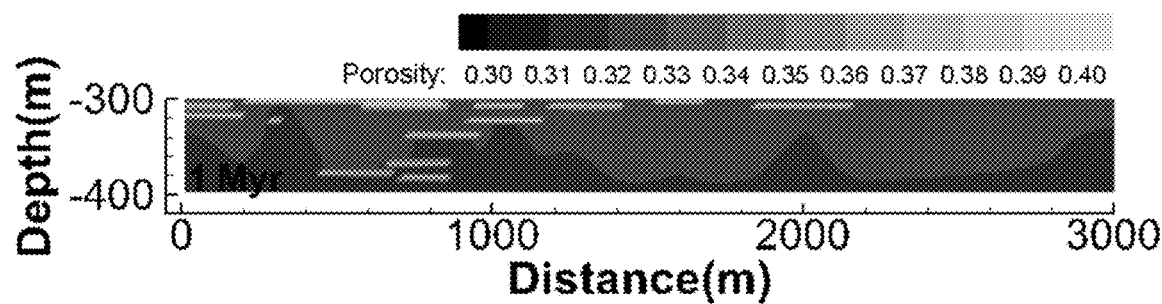
FIGS. 2-9 are schematic diagrams of the porosity distribution over time in two-dimensional space during the sediment of carbonate rock in Example 1.
Figure 3:
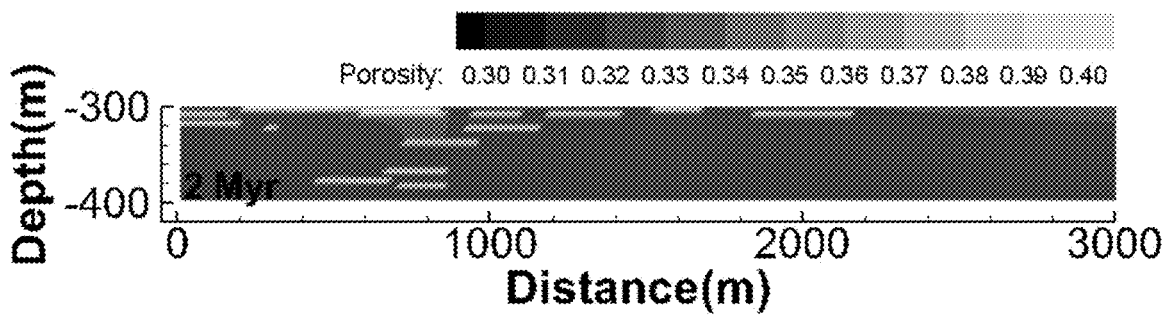
Figure 4:
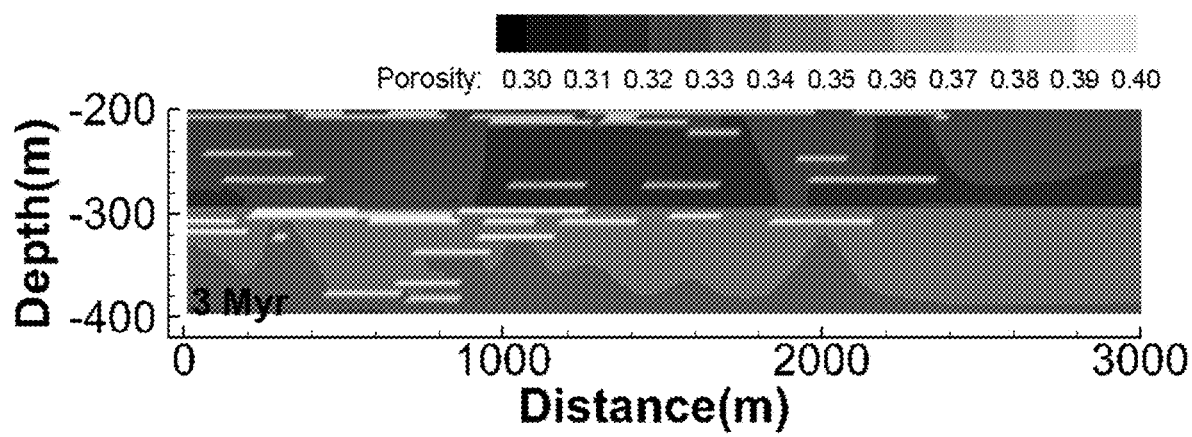
Figure 5:
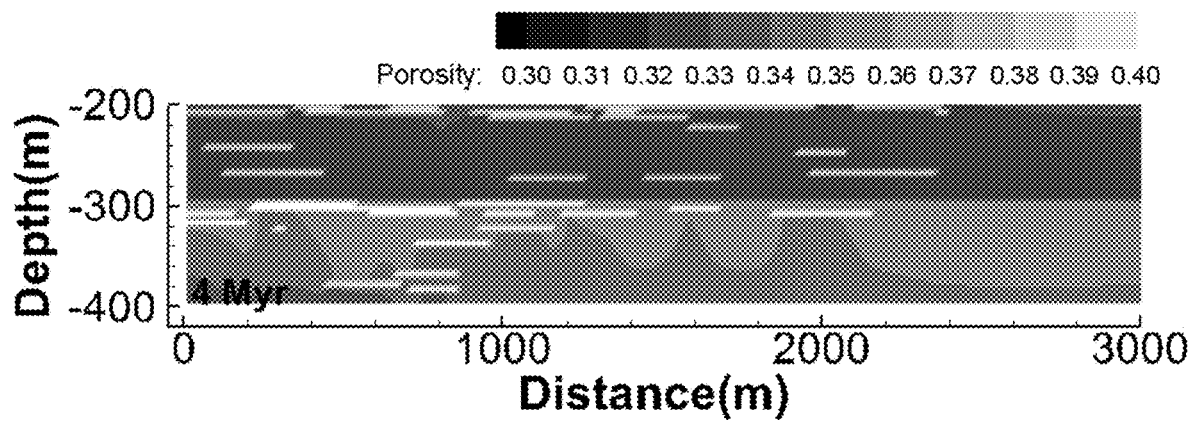
Figure 6:
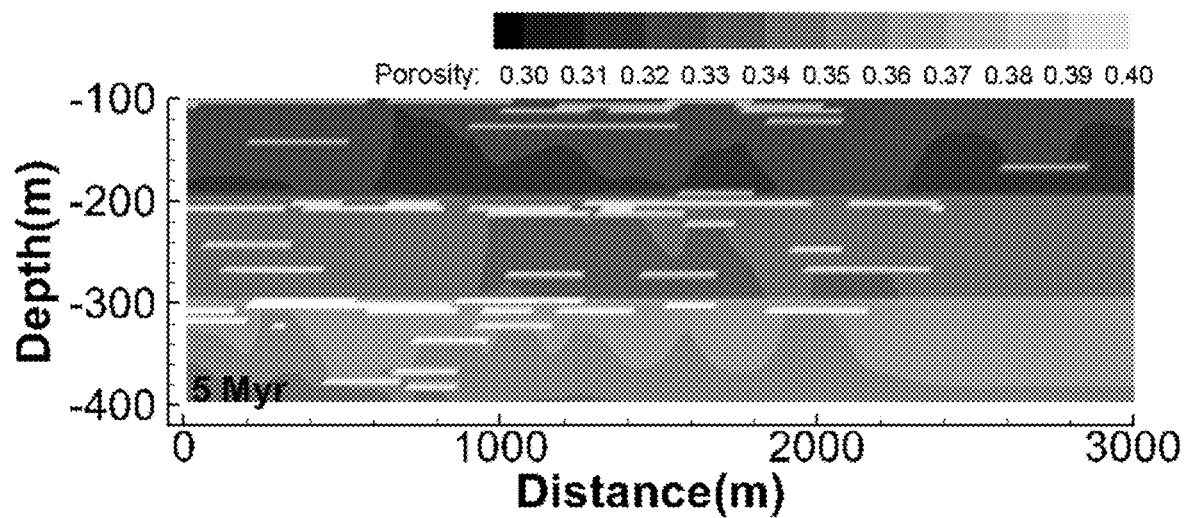
Figure 7:
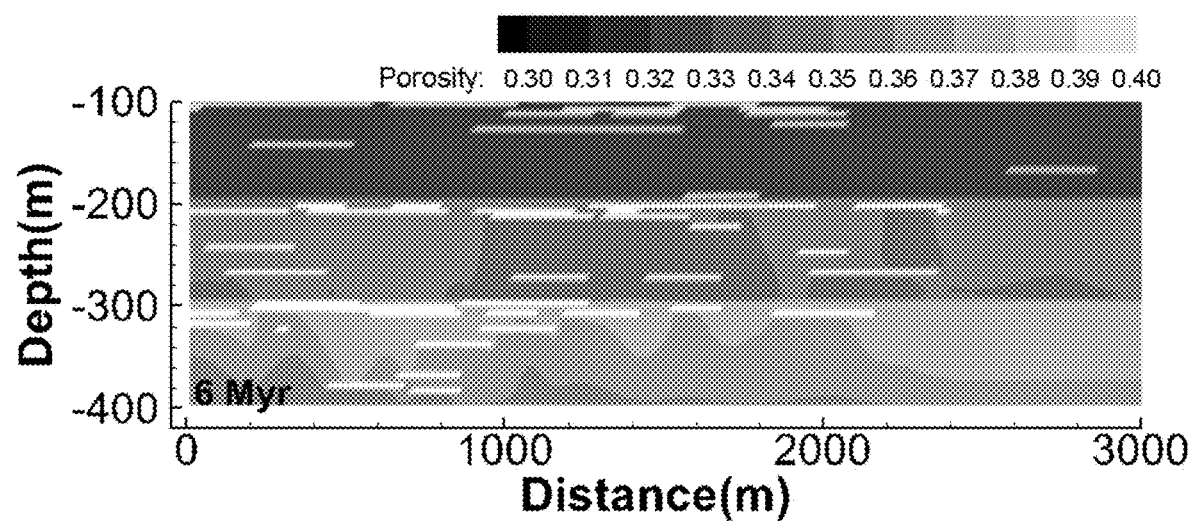
Figure 8:
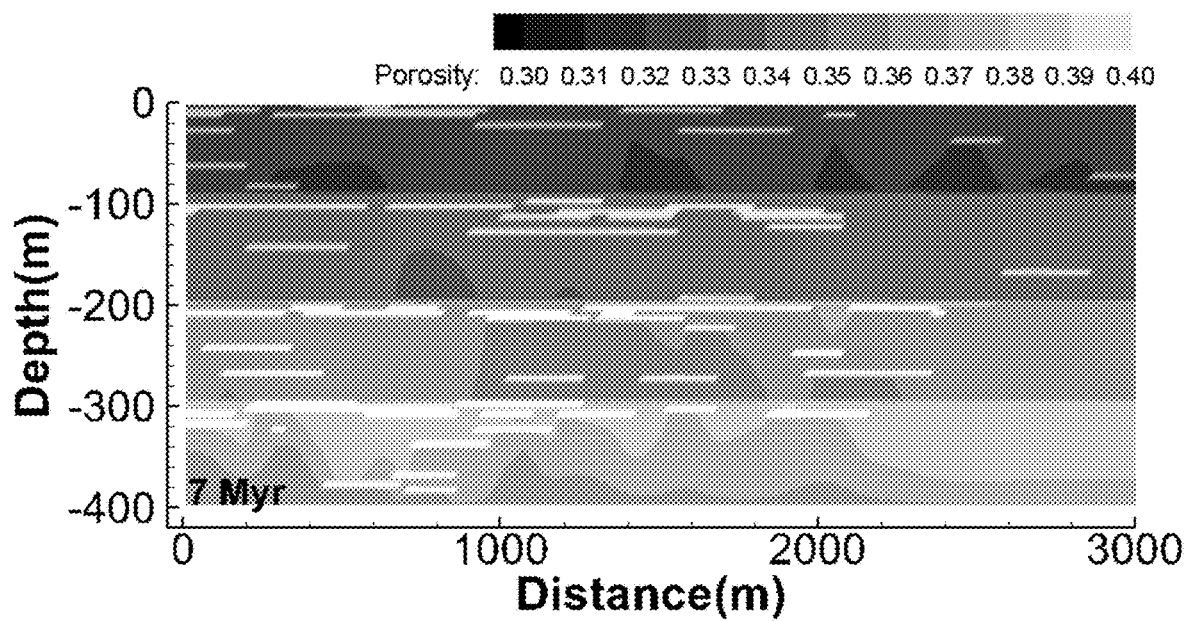
Figure 9:
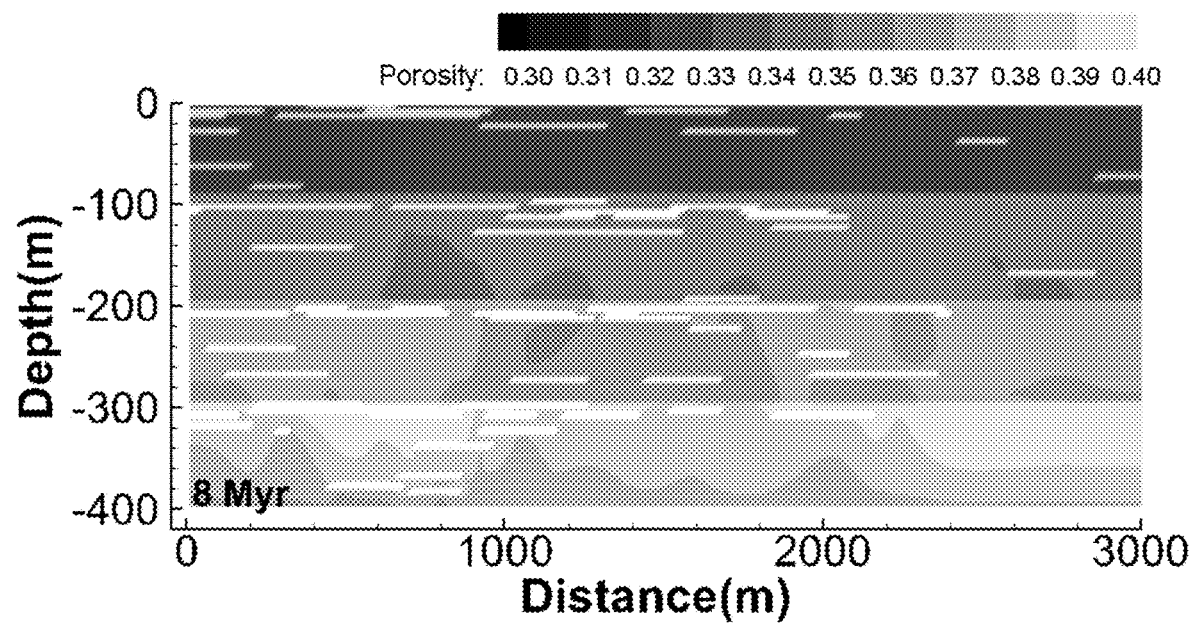
Figure 10:
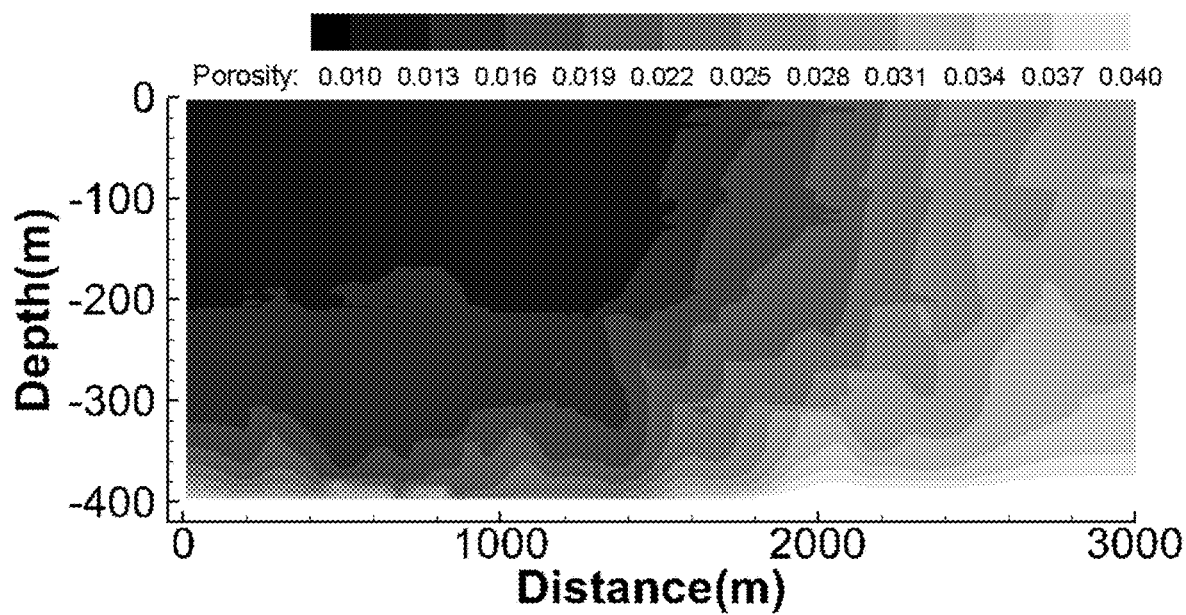
FIG. 10 is a schematic diagram of the porosity distribution of the carbonate rock reservoir in two-dimensional space in Example 1.

As can be seen from FIG. 10, it is believed that four major phases of large-scale sea level rise and fall occurred in the area, forming three third-order sequence boundaries, each sequence with a formation time of about 2 to 3 Myr. The thickness of Yingshan Formation in Taichung area is 350 to 700 m. In the simulation, the sequence stratigraphic model is simplified in order to simplify the calculation volume. The formation time of the sequence was set to be 2 Myr, with 1 Myr in the sedimentary phase and the other 1 Myr in the exposure phase where no sediment occurred. The model sedimentation thickness was determined to be about 400 m based on the main sedimentation rate of 100 m/Myr for 1Myr carbonate rock.

(2) Thin section, scanning electron microscopy, fluid inclusion, cathodoluminescence and carbon and oxygen isotope essay analyses were conducted to analyze the Ordovician carbonate rock in Shunnan area to determine the diagenetic evolution of the reservoir, determine the typical diagenetic events according to the degree of influence on the reservoir porosity, and dividing the diagenetic stages of the reservoir into six successive diagenetic stages, namely sedimentary-penecontemporaneous stage, penecontemporaneous-shallow burial stage, epigenetic stage, shallow burial stage, middle-deep burial stage and deep burial stage.

(3) A geological model with a sea level rise and fall cycle of 2 Myr, a sediment rate of 100 m/Myr, a total simulated thickness of 400 m, and a sediment period of 8 Ma was established based on the information in step (1). Based on the reactive solute transport simulation software TOUGHREACT, the diagenesis and porosity evolution with increasing reservoir thickness and continuous superposition of multiple reservoirs during the cyclic sea level rise and fall were simulated. The stratigraphic physical parameters in the model are shown in Table 1.

TABLE 1

| Parameters | Values |
| --- | --- |
| Porosity % | 30, 35 |
| Horizontal permeability mD | 40, 120 |
| Vertical permeability e mD | 40, 120 |
| Compression coefficient $Pa^{-1}$ | $4.5 \times 10^{-10}$ |
| Rock density $kg \cdot m^{-3}$ | 2710 |
| Thermal conductivity $W/(m \cdot °C.)$ | 2.20 |
| Rock particle specific heat $J/(kg \cdot °C.)$ | 852 |

The cyclic sea level rise and fall process during sediment was divided into four substages of continuous diagenetic evolution. During the sea level rise, the reservoir is mainly located below the sea level and is affected by rapid transgression, and a new set of reservoir is deposited on top of the original sediment; during the sea level fall, the reservoir is exposed above the sea level and the sediment receives the leaching and dissolution of meteoric freshwater. The sediment thickness and diagenetic time for the whole sedimentary diagenetic evolution are shown in Table 2.

TABLE 2

Summary of sedimentary diagenetic evolution process

| Diagenetic time/Myr | Sediment period | Denudation period | Sediment thickness/m |
| --- | --- | --- | --- |
| 1 |  | ✓ | 100 |
| 2 | ✓ |  | 100-200 |
| 3 |  | ✓ | 200 |
| 4 | ✓ |  | 200-300 |
| 5 |  | ✓ | 300 |
| 6 | ✓ |  | 300-400 |
| 7 |  | ✓ | 400 |
| 8 | ✓ |  | 400 |

FIGS. 2-9 are schematic diagrams of the porosity distribution over time in two-dimensional space during the sedimentary diagenetic evolution of carbonate rock in Example 1, which fully reflect the non-homogeneous distribution of porosity in carbonate rock reservoirs caused by meteoric freshwater leaching. Meanwhile, due to the regular rise and fall of sea level, the sequence superposition of carbonate rock reservoirs has a certain pattern. Due to the action of meteoric freshwater, FIGS. 2-9 also reflect the non-homogeneity of the porosity distribution of the sequences in the vertical direction.

(4) Using the simulation result in step (3) as the initial value for the simulation of diagenetic evolution, the diagenetic evolution of six diagenetic stages, namely sedimentary-penecontemporaneous stage, penecontemporaneous-shallow burial stage, epigenetic stage, shallow burial stage, middle-deep burial stage and deep burial stage, was simulated in stages and continuously, and the porosity evolution in space over time was calculated. The results are shown in FIG. 10.

FIG. 10 is a schematic diagram of the porosity distribution of the carbonate rock reservoir in two-dimensional space in Example 1. Based on the distribution of porosity and mineral content in FIG. 9, a next-stage diagenetic evolution of six diagenetic stages including sedimentary-penecontemporaneous stage, penecontemporaneous-shallow burial stage, epigenetic stage, shallow burial stage, middle-deep burial stage and deep burial stage was carried out, and the distribution of porosity on a two-dimensional plane was finally obtained.

What is claimed is:

1. A method for recovering a porosity evolution process of sequence stratigraphy of carbonate rocks, wherein the method comprises:
   a step of establishing a sequence stratigraphic framework of carbonate rocks, comprising: recovering paleoclimate and paleo-sea level from geological, geochemical and geophysical data and identifying a sequence boundary in conjunction with a regional geological setting to establish the sequence stratigraphic framework of carbonate rocks; wherein, the geochemical and geophysical data comprise core, thin section and logging information;
   a step of dividing diagenetic stages, comprising: determining a diagenetic sequence by thin section, scanning electron microscopy, fluid inclusion, cathodoluminescence and carbon and oxygen isotope assay analysis, determining the diagenetic evolution process of the reservoir, and determining typical diagenetic events and dividing diagenetic stages based on the degree of influence on the reservoir porosity;
   a step of simulating diagenesis and porosity evolution with increasing reservoir thickness and continuous superposition of multiple reservoirs during cyclic rise and fall of sea level to obtain a simulation result, comprising simulating, based on a reactive solute transport simulation program, the diagenesis and porosity evolution with increasing reservoir thickness and continuous superposition of multiple reservoirs during cyclic rise and fall of sea level, according to a superposition pattern of carbonate rock sequence in vertical direction;
   a step of calculating the porosity evolution in space over time by using the simulation result as initial values for simulation of diagenetic evolution process and simulating in stages and continuity the multi-stage diagenetic evolution process that the carbonate rock strata undergo after sediment based on the divided diagenetic stages; and finally obtaining the distribution of porosity on a two-dimensional plane.

2. The method according to claim 1, wherein the method comprises using sequence stratigraphy and sedimentary petrology as a guide to recover the paleoclimate and paleo-sea level from geological, geochemical and geophysical data and identifying the sequence boundary in conjunction with the regional geological setting to establish the sequence stratigraphic framework of carbonate rocks.

3. The method according to claim 1, wherein the simulation program is a numerical software for simulation of diagenetic effects.

4. The method according to claim 1, wherein the simulation program is TOUGHREACT or TOUGHSTONE.

5. The method according to claim 1, wherein the superposition pattern of carbonate rock sequence in vertical direction is to determine the timing of the cyclic rise and fall of the sea level, to determine the sediment thickness of the reservoir for each cycle, and to determine the sediment properties of each sequence, in conjunction with the established sequence stratigraphic framework of carbonate rocks, so as to establish a geological model to simulate the diagenesis and porosity evolution.

6. The method according to claim 5, wherein the stratigraphic physical parameters of the geological model are selected from the groups consisting of rock porosity, rock horizontal permeability, rock vertical permeability, rock compression coefficient, rock density, rock thermal conductivity, and rock particle specific heat.

\* \* \* \* \*